(12) United States Patent
Howard et al.

(10) Patent No.: US 10,716,792 B2
(45) Date of Patent: Jul. 21, 2020

(54) NEUROQUIESCENCE—A TREATMENT FOR NEUROLOGICAL AND NERVOUS SYSTEM BIOELECTRICAL DYSREGULATION ASSOCIATED WITH SEIZURES OF EPILEPSY

(71) Applicants: Gary Aaron Howard, Eagan, MN (US); Debora Zucco Sassi Yonezawa Siviglia, Lorraine (FR)

(72) Inventors: Gary Aaron Howard, Eagan, MN (US); Debora Zucco Sassi Yonezawa Siviglia, Lorraine (FR)

( * ) Notice: Subject to any disclaimer, the term of this patent is extended or adjusted under 35 U.S.C. 154(b) by 0 days.

(21) Appl. No.: 16/698,444

(22) Filed: Nov. 27, 2019

(65) Prior Publication Data

US 2020/0171045 A1 Jun. 4, 2020

Related U.S. Application Data

(60) Provisional application No. 62/772,811, filed on Nov. 29, 2018.

(51) Int. Cl.
| | | |
|---|---|---|
| *A61K 31/551* | (2006.01) | |
| *A61K 31/5513* | (2006.01) | |
| *A61K 9/00* | (2006.01) | |
| *A61P 25/08* | (2006.01) | |
| *A61K 31/445* | (2006.01) | |

(52) U.S. Cl.
CPC ........ *A61K 31/5513* (2013.01); *A61K 9/0019* (2013.01); *A61P 25/08* (2018.01)

(58) Field of Classification Search
CPC .......................... A61K 31/445; A61K 31/551
USPC ................................................. 514/220, 317
See application file for complete search history.

(56) References Cited

U.S. PATENT DOCUMENTS

| | | | |
|---|---|---|---|
| 6,015,557 A | 1/2000 | Tobinick et al. | |
| 6,177,077 B1 | 1/2001 | Tobinick | |
| 6,419,934 B1 | 7/2002 | Tobinick | |
| 6,419,944 B2 | 7/2002 | Tobinick | |
| 6,537,549 B2 | 3/2003 | Tobinick | |
| 6,936,605 B2* | 8/2005 | March ................... | A61K 9/006 514/220 |
| 6,982,089 B2 | 1/2006 | Tobinick | |
| 7,214,656 B2 | 5/2007 | Tobinick | |
| 8,765,125 B2 | 7/2014 | Skokos | |
| 2004/0138238 A1 | 7/2004 | Dhanoa et al. | |
| 2008/0103179 A1 | 5/2008 | Tam et al. | |
| 2014/0057885 A1* | 2/2014 | Reddy .................. | A61K 31/573 514/182 |

OTHER PUBLICATIONS

Dutchen, Stephanie, "Scientists pinpoint neural activity's role in human longevity," The Harvard Gazette, Oct. 16, 2019, 4 pages.
Heard et al,, "Sedation and Analgesia," Pediatric Critical Care (Fourth Edition), 2011, p. 1673.
Notification of Transmittal of the International Search Report and Written Opinion, PCT/US2019/063748, dated Feb. 20, 2020, 7 pages.
Ives, James, "UCPH research receives prize for research into brain's cleaning system," www.news-medical.net/news/20181108/UCPH-researcher-receives-prize-for-r, Retrieved.from the Internet Mar. 17, 2020.
Lenz et al., "Systemic thrombin inhibition ameliorates seizures in a mouse model of pilocarpine-induced status epilepticus," Journal of Molecular Medicine, Nov. 2019, vol. 97, issue 11. pp. 1567-1574.
"Longevity Linked to Proteins That Calm Overexcited Neurons," https://www.quantamagazine.org/longevity-linked-to-proteins-that-calm-overexcited-neurons-20191126/, Retrieved from the Internet Mar. 17, 2020.
Manno et al., "New Management Strategies in the Treatment of Status Epilepticus," Mayo Clinic Proceedings, 2003, vol. 78, issue 4, p. 508.
"Neurons energy organelle protected from damage linked to ALS & Alzheimer's", https://neurosciencenews.com/mitochondria-als-alzheimers-15457/, Retrieved from the Internet Mar. 17, 2020.
Scientists solve century-old neuroscience mystery; answers may lead to epilepsy treatment, www.eurekaalert.org/pub-releases/2018-11/vt-ssc110618.php, Retrieved from the Internet Mar. 17, 2020.
Shorvon et al., The treatment of super-refractory status epilepticus: a critical review of available therapies and a clinical treatment protocol. Brain, 2011. pp. 1-17.
Todididk et al., "Rapid cognitive improvement in Alzheimer's disease following perispinal etarterctpt administration," Journal of Neuroinflarnmation, 5(2). Jan. 9, 2008, 10 pages.
Tobinick, Edward, "Perispinal etanercept: a new therapeutic paradigm in neurology," Expert Rev. Neurother., 10(6), 2010, pp. 985-1002.
Yin et al, "Chemical Conversion of Human Fetal Astrocytes into Neurons through Modulation of Multiple Signaling Pathways," Stem Cell Reports, vol. 12, Mar. 5, 2018, pp. 488-501.

* cited by examiner

*Primary Examiner* — Raymond J Henley, III
(74) *Attorney, Agent, or Firm* — Stanek Lemon Crouse & Meeks, PA

(57) ABSTRACT

The present inventive concept describes a method for treating the neurovascular disruption underlying Epileptic Seizures and other traits of Epilepsy and Infantile Spasms by improving the neurophysiological environment and then enabling by sustained sedation a biomechanism of glial cells for neuronal repairs.

20 Claims, No Drawings

NEUROQUIESCENCE—A TREATMENT FOR NEUROLOGICAL AND NERVOUS SYSTEM BIOELECTRICAL DYSREGULATION ASSOCIATED WITH SEIZURES OF EPILEPSY

CROSS-REFERENCE TO RELATED APPLICATIONS

This application claims the benefit of U.S. Provisional Patent Application Ser. No. 62/772,811, filed Nov. 29, 2018, the entirety of which is incorporated herein by reference.

FIELD

The present inventive concept relates to and describes functions of treatment to enable healing the bioelectrical noise underlying seizures associated with Epilepsy, such as: Benign Rolandic Epilepsy of Childhood; Absence Epilepsy; Juvenile Myoclonic Epilepsy; Benign Occipital Epilepsy; Lennox-Gastaut syndrome; and SCN2A encephalopathy.

BACKGROUND

Epilepsy is a central nervous system (neurological) disorder in which brain activity becomes abnormal, causing seizures or periods of unusual behavior, sensations, and sometimes loss of awareness. Not all seizures are due to epilepsy; other conditions that can look like epilepsy include hypoglycemia. In this present inventive concept, the term "seizure" refers to neuronal bioelectrical activity induced seizures of Epilepsy.

Deficiencies in microvascular bloodflow agitate neurons, causing them to invest their energy in bioelectrical signaling to stimulate vascular support, bringing vascular transport of oxygen; this neuronal agitation serves a purpose for their survival. If the neuron's need for more oxygenation through bloodflow becomes quenched, the bioelectrical agitation was successful, and the neuron becomes stable. If there is a delay in successful oxygenation of an agitated neuron, the bioelectrical agitation may stimulate even well-oxygenated neurons to connect in unproductive circuits without appropriate inhibitory and excitatory links.

The bioelectrical pulsing synchronizes within the interconnected cluster of neurons, thereby increasing the amplitude of the neuroelectromagnetic field measured on an electroencephalogram (EEG). There may be few neurons agitated by low bloodflow and deficient oxygenation, but their interconnected circuit of synchronized hyperactivity exhausts the bloodflow supply of oxygen which may stress vascular capacity and leave other neurons in an oxygenation deficit.

Cerebrovascular resilience supports oxygenation of neurons. Deficiencies in cerebral bloodflow or microvascular support of neurons increases their agitated activity. Neuronal agitation activity exhausts oxygen levels which are already low, and surrounding neurons become agitated. Febrile illness or strenuous exercise when in a constricted bloodflow state can induce exhaustion of oxygen levels at the neurons thereby stimulating neuronal agitation. Inconsistent microvascular transport of oxygen increases inflammation around the neurons thereby inhibiting potential healing.

Immunoinflammatory imbalance associated with diminished oxygenation during sleep is a threat to neuronal health. Oxygen transfer deficiencies in lungs to vascular transport and into microvascular support of neurons decreases during sleep thereby increasing risks of seizures. During sleep, autoregulation reduces bloodflow which increases risk of low oxygenation to neurons which may be above the threshold needed to avoid agitation during the day. Sleep issues such as restless leg syndrome may be indicative of deficiencies in oxygenation to the sensory neurons in the legs, and over time these neurons may become hyperactive and produce sustained itchiness or other symptoms.

As with the root-cause of epilepsy, the central nervous system influenced by immunological and vascular distress stimulate neurons outside the brain to agitation. Resolving these root-causes and the neurovascular inflammation around the central nervous system is required to potentially provide healing, otherwise those neurons will again over time become noisy, resulting in pain and other signaling dysregulations.

As such, there remains a need for improved methods and protocols for resolving disorders related to bioelectrical dysregulation in neurons, such as epilepsy and seizures associated with epilepsy.

SUMMARY

The present inventive concept is related to resolving and healing bioelectrical dysregulation of neurons that induce seizures associated with epilepsy. The protocol we named "Neuroquiescence" is the process of using sustained sedation to enable glial biomechanisms maximum capacity for neuronal healing, remyelination, pruning, and disconnections of maladapted circuits formed due to agitated neurons. Neuroquiescence as described herein is safe because it was designed for babies, and has been used for over 200 neonates, infants, toddlers, children, and teenagers, for whom over 95% of cases resolved of all symptoms of Epilepsy, including the neurophysiological root-cause, thereby enabling a trajectory away from any risk of any return of bioelectrically agitated neurons.

According to an aspect of the inventive concept, provided is a method for enabling the glial cells to heal the neuronal maladaptations and the demyelinating effects of seizures associated with an epileptic disorder in a subject in need thereof comprising: preparing cerebrovascular robustness of bloodflow and oxygenation, and then medically sedating the subject for a sustained period of time by administering a therapeutically effective amount of an anesthetic, wherein the sedating of the subject pauses bioelectrical activity of neurons in the subject to facilitate healing of the neurons in the subject.

According to another aspect of the inventive concept, provided is a method for treating irregular, abnormal, or excessive neuronal activity associated with an epileptic disorder in a subject in need thereof comprising: medically sedating the subject for a sustained period of time by administering a therapeutically effective amount of an anesthetic, wherein the sedating of the subject pauses bioelectrical activity of neurons in the subject to facilitate healing of the neurons in the subject.

According to yet another aspect of the inventive concept, provided is a method of pausing bioelectrical activity in neurons in a subject suffering from an epileptic disorder comprising: medically sedating the subject for a sustained period of time by administering a therapeutically effective amount of an anesthetic, wherein the pausing of bioelectrical activity facilitates healing of neurons exhibiting irregular, abnormal, and/or excessive activity.

DETAILED DESCRIPTION

In the following detailed description, embodiments of the present inventive concept are described in detail to enable practice of the invention. Although the invention is described with reference to these specific embodiments, it should be appreciated that the invention can be embodied in different forms and should not be construed as limited to the embodiments set forth herein. Rather, these embodiments are provided so that this disclosure will be thorough and complete, and will fully convey the scope of the invention to those skilled in the art. All publications cited herein are incorporated by reference in their entireties for their teachings.

The invention includes numerous alternatives, modifications, and equivalents as will become apparent from consideration of the following detailed description.

Unless otherwise defined, all technical terms used herein have the same meaning as commonly understood by one of ordinary skill in the art to which this disclosure belongs.

Also as used herein, the terms "treat," "treating" or "treatment" may refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

As used herein, the terms "prevent," "preventing" or "prevention of" (and grammatical variations thereof) may refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the term "prevent," "preventing," or "prevention of" (and grammatical variations thereof) refer to prevention and/or delay of the onset and/or progression of a metabolic disease in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

An "effective amount" or "therapeutically effective amount" may refer to an amount of a compound or composition of this invention that is sufficient to produce a desired effect, which can be a therapeutic and/or beneficial effect. The effective amount will vary with the age, general condition of the subject, the severity of the condition being treated, the particular agent administered, during the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, The Science and Practice of Pharmacy (latest edition)).

The Need for Neuroquiescence

Neuroquiescence is a procedure, a protocol used by specialized neurologists, anesthesiologists and radiologists; there are no new medications required as we use only existing FDA-approved medications and equipment.

Neuroquiescence improves cerebrovascular bloodflow to a robust level, and then pausing the affected neurons' bioelectrical activity for glial cell repairs. As initially envisioned, this protocol would mitigate the root-cause and run the pathogenesis of Epilepsy in reverse. The development of Neuroquiescence is rooted in the following conceptualization of the pathogenesis of Epilepsy:

Cerebral electrical activity (whether bioelectrical or artificial) stimulates bloodflow.

Deficiencies in microvascular bloodflow agitate neurons for bioelectrical signaling to stimulate vascular support for transport of oxygen; this neuronal agitation serves a purpose for their survival.

If the neuron's expending bioelectrical energy for more oxygenation through bloodflow succeeds, the neuron becomes stable.

If the neuron's expending bioelectrical energy for more oxygenation through bloodflow is not successful, the bioelectrical agitation may stimulate even well-oxygenated neurons toward dysfunctional interconnections without appropriate inhibitory and excitatory links.

Bioelectrically-saturated neurons can become locked into a dysregulated feedback-loop that expends all the neuron's energy capacity while also disabling pruning and glial assistance in remyelinating. Bioelectrical pulsing synchronizes within the interconnected cluster of neurons, thereby increasing the amplitude of the neuroelectromagnetic field measured on EEG, and further exhausting the energy available in bloodflow and glial support.

Even a low quantity of neurons agitated by low bloodflow and deficient oxygenation may interconnect into dysfunctional circuits of synchronized neuronal activity, thereby exhausting the local bloodflow supply of oxygen, stressing vascular capacity, leaving otherwise healthy neurons in an oxygenation deficit.

A circular feedback-loop of maladaptively interconnected neurons may be susceptible to oscillation even after the microvessels and cerebrovascular bloodflow have improved.

When later observed, vascular health in this region of neuronal agitation may appear nominal because it had time to improve in response to the agitated bioelectrical activity. Still, there may be deficient bloodflow and oxygenation for the neurons to disconnect from their maladaptive interconnections and heal, even when we pause their bioelectrical activity. We therefore improve their microvascular environment.

Evidence that the neurogenesis of Epilepsy is about cerebrovascular connectivity to microvessels for oxygenation of neurons by robust bloodflow is made apparent in the difference between the first-week sedation to ease the removal of antiseizure medications versus the sixth-week results of sedation after the cerebrovascular bloodflow is made more robust.

In week one with a patient, all antiseizure medications are removed and an initial sedation session of six days is only for easing this transition of their nausea and their constant seasickness feeling.

Even after week-one of Dobutamine and a six-day initial sedation, 10% to 15% of our children were resolved of not only their seizures, but their neuronal agitation noise as well never returned.

Weeks two through five are our Pre-Neuroquiescence preparations of cerebrovascular bloodflow and oxygenation, and there is typically no sedation and never any antiseizure medication. For those at risk of seizures, the initial sedation session was extended through week six so that the Dobutamine had time to avail better bloodflow for those agitated neurons. For about 80% of our children, although there were no seizures, the neuronal agitation noise was still present.

In week-six (or a few weeks later if cerebrovascular bloodflow is not yet robust) the patient was subjected to the Neuroquiescence sedation session, resulting in over 95% of our children having no neuronal agitation noise, and it never returns; their brains continue becoming healthier as we continue the Dobutamine, the EEG monitoring, and the fMRI monitoring are continued as part of a post-sedation period.

The only difference between week-one and week-six is the duration of time our children had on Dobutamine for producing a robust cerebral bloodflow. Robust oxygenation with robust cerebral bloodflow are indicated in the comparison between week-one versus week-six as fundamental to the root-cause of Epilepsy, and therefore fundamental to the environment supporting the self-mitigation of neuronal maladaptations.

The objective of this treatment is to enable glial cells to assist agitated and hyperactive neurons to remyelinate and reset to cellular homeostasis. While glial cells persistently strive to accomplish this in normal neuronal function, glial cells cannot keep up during a neuronal dysregulated state of saturated bioelectrical activity, so remyelinating and perhaps pruning cannot occur. Achieving healing of agitated neurons requires that their bioelectrical activity be paused.

Cerebrovascular resilience supports oxygenation of neurons. Deficiencies in cerebral bloodflow or microvascular support of neurons increases their agitated activity. Neuronal agitation activity exhausts oxygen levels which are already low, and surrounding neurons become agitated. Febrile illness or strenuous exercise when in a constricted bloodflow state can induce exhaustion of oxygen levels at the neurons thereby stimulating neuronal agitation. Inconsistent microvascular transport of oxygen increases inflammation around the neurons thereby inhibiting healing.

Immunoinflammatory imbalance associated with diminished oxygenation during sleep is a threat to neuronal health. Oxygen transfer deficiencies in lungs to vascular transport and into microvascular support of neurons decreases during sleep thereby increasing risks of seizures. During sleep, autoregulation reduces bloodflow which increases risk of low oxygenation to neurons which may be above the threshold needed to avoid agitation during the day. Sleep issues such as restless leg syndrome may be indicative of deficiencies in oxygenation to the sensory neurons in the legs, and over time these neurons may become hyperactive and produce sustained itchiness or other symptoms.

Those with a chronic asthma or bronchitis are more susceptible to risk of neuropathic pain later in life due to deficiencies in oxygenation for sensory neurons, and as children are more likely to have issues such as stuttering of speech or auditory agnosia due to decreased oxygenation in regions of the brain.

Genetic factors increase neurophysiological distinctions that expose susceptibility to "mitochondrial Epilepsy" induced by cerebral vasospasm or pulmonary vasospasm and factors influencing bloodflow and oxygen-transfer efficiencies. These genetic factors can be overwhelmed by our changing the environment before neuronal bioelectrical activity becomes disruptive by preemptively applying vasodilation and oxygenation functions of our protocol. We can also pause neuronal bioelectrical activity to allow healing of the maladapted cells if preemptive intervention was too late.

In some embodiments, the subject may be medically sedated deeply enough to pause bioelectrical activity for a continuous and sustained period of a minimum of three days for enabling glial cells their neuronal repairs and remyelination.

Pausing of, for example, bioelectrical activity of neurons, as will be appreciated by one of skill in the art, may be defined as the reduction of amplitude and/or frequency of bioelectrical waveforms associated with electrical activity of neurons. The pausing of bioelectrical activity may be monitored, for example, by an electroencephalogram (EEG). The bioelectrical waveforms that are paused according to embodiments of the present inventive concept may be abnormal bioelectrical waveforms associated with neurological disorders, such as epilepsy.

Healing of, for example, neurons, according to embodiments of the present inventive concept, as will be appreciated by one of skill in the art, may be defined as the restoration of normal function of neurons that exhibit irregular, abnormal, and/or excessive bioelectrical activity, such as may be manifested as part of a neurological disorder, such as epilepsy.

It will be appreciated that monitoring of bioelectrical activity of neurons during medical sedation for a sustained period of time may be performed to assess the extent of healing of neurons in a subject, and the period of time for medical sedation may be adjusted depending upon the extent of healing which takes place during medical sedation.

Embodiments of the present inventive concept include: Vasodilation as Prophylaxis for Infantile Spasms and Epilepsy; Neuroquiescence for Epilepsy in Children; and Neuroquiescence for Epilepsy in Adults.

Medications

The Neuroquiescence Protocol defines functions of medications and not specific medications, although the medications listed are the ones we have used, it is by no means intended to be limited thereto. All medications used according to the present inventive concept are selected based upon their approved function; immunoinflammatory medications or oxygenation medications or anesthesia medications are so chosen for their known and approved functions.

Exemplary medication schedules of a Neuroquiescence protocol are set forth as follows. An overview of an exemplary protocol including: week one of sustained sedation and removal of antiseizure medications; a number of weeks (weeks two through five, for example, in children, longer in adults) as part of a preparation period with vasodilation and oxygenation and with no sedation and no antiseizure medication; a second Neuroquiescence/sedation session at week six (later for adults, for example nine weeks); and a post-sedation period with medications for vasodilation and oxygenation are outlined in Table I. Use of Midazolam (anesthesia) for an exemplary six-day extended Neuroquiescence/sedation session is outlined in Table II. Prior to a Neuroquiescence Protocol and/or during the first week of the protocol, the patient should be removed from any of the existing anti-seizure medication, such as Tegretol, Tegretol XR, Carbatol, Equetro, Teril, Diazepam, Phenytoin, Carbamazepine, Valproic Acid, Ethosuximide, etc.

Vasodilation Function: A Medication-Induced Improvement in Vascular Capacity and Throughput of Bloodflow Vasodilation has proven to be an element in resolving agitated neurons, better improving bloodflow and oxygenation. We have two sedation periods, week-one and week-six. Only about 20% of cases come out of week-one with no return of neuronal agitation, but after the vasodilation medication has an opportunity to work, 95% come out of the sixth week Neuroquiescence session with no return of the neuronal agitation.

Brainscans for evaluation of Cerebral Bloodflow (CBF) and Intracranial Pressure (ICP) are required for determining which of two vasodilation medications fit the need.

Dobutamine: when the spatial area of impeded bloodflow is larger; this also used as an ongoing maintenance vascular dilation medication.

Prostin: for neonates with small spatial area of impeded bloodflow; Prostin also may be useful for older patients where bloodflow is good but oxygenation is still deficient. Prostin is not used in ongoing maintenance because of the need for persistent monitoring for risk of cerebral-bleeding and/or congestive heart failure and/or hypertension.

Oxygenation Function: A Medication-Induced Improvement in the Oxygen Transfer Functions and Transport Levels in the Blood The oxygen transfer efficiency of the entire respiratory system must be confirmed, from the secure airway, through blood-oxygen levels, through appropriate brain oxygenation.

A supplemental oxygen pediatric nasal mask is recommended during sedation for Neuroquiescence, thereby providing a more comfortable fit and improved respiratory support yielding oxygenation saturation of 90% to 94%.

Especially for children diagnosed with chronic Asthma or Bronchitis and cases wherein oxygenation is most challenged, we have combined the IV-based oxygenation medication with the oxygen mask, and only under close medical supervision monitoring blood-oxygen levels.

Nasal Mask:

Ipratropium (inhalation)

Respiratory anticholinergic—Ipratropium. Tiotropium or Aclidinium

Short duration: Beta-2 Agonist; bronchial relaxant (not to exceed 30 mcg per day). Albuterol, and Levalbuterol.

Long duration oral or IV: increased selectivity in neuroreceptors; long acting Beta-2 Agonist; relaxes bronchial smooth muscle by acting selectively on Beta-2 receptors; heartrate may be slowed. Salmeterol. Formoterol, Arformoterol, Vilanterol, Indacaterol, and Xanthine's (derivatives).

Counterinflammation Function: A Medication-Induced Reduction of Inflammatory Impediments to Oxygenation and Healing of Neurons Anti-inflammatory medications Cyclophosphamide and Ketoprofen are used in alternating weeks. Cyclophosphamide; IV or PO (oral); daily 8 to 20 mg per kg, and Ketoprofen; IV or PO (oral); 75 mg per kg PO over q8 hr or 50 mg per kg PO q6 hr Neuroquiescence Function: A Medication-Induced Sedation Sustained to Pause Bioelectrical Activity of Neurons for their Healing Note: This procedure shall never be used except under the guidance of an anesthesiologist with EEG monitoring plus and all standard critical functions monitoring.

Midazolam IV dosage at 0.2 mg/kg (Maximum 10 mg) is effective in termination of frequency of seizure and Grand mal seizure associated with loss of consciousness and other neuropathology. Midazolam is well absorbed when administered by IV, but it is necessary to be prepared to assist with ventilations especially if the patient has a history of brain trauma.

An allergy test is required before the Neuroquiescence session, and we find that approximately 5% are allergic to Midazolam. Neuroqxuiescence Protocol therefore uses Fentanyl dosage 2-3 mcg/kg IV as an optional sedation medication in case of the patient present positive test result for allergic reaction to Midazolam. Fentanyl compounds are safe and can reduce complications associated with allergic site.

Midazolam Sedation—Pediatric

Refer to Table II. for use of intravenous IV-delivered Midazolam for the Neuroquiescence session. There are six days listed with an initial dose each day followed by the hourly dose listed by bodyweight. The objective is to safely keep the patient deeply sedated enough to pause neuronal bioelectrical activity. If the maximum dose of 5 mcg/kg/min does not achieve control, General Anesthesia with Thiopentone will be required. Pulse Oximetry is mandatory. Establishing the infusion rate of between one and five micrograms per kilogram per minute is a dynamic process with monitoring the EEG for neuronal bioelectrical agitation activity.

Cautions

Macrolides (Erythromycin, Clarithromycin)—inhibit metabolism of Midazolam, and cause excess sedation to occur Phenytoin—Midazolam may make levels unpredictable (decrease or increase phenytoin levels)

Baclofen—Midazolam is also a muscle relaxant and can cause excessive muscle relaxation with Baclofen IV Fentanyl—Continuous Sedation/Anesthesia In the rare case where a patient is allergic to Midazolam, another anesthetic, for example, Fentanyl, may be used and with which similar results as with Midazolam have been exhibited. It will be appreciated by one of skill in the art that more options for anesthesia are available, especially if a patient is allergic to both Midazolam and Fentanyl, and due to decreasing availability of Fentanyl due to misuse.

Methods to induce Neuroquiescence, according to embodiments of the present invention, may include medically sedating a subject by administering a therapeutically effective amount of an anesthetic, for example, but not limited to, midazolam. The medical sedation may take place continuously, for example, over a period of time of about 1 day, 2 days, 3 days, 4 days, 5 days, 6 days, or 7 days (1 week). Midazolam may be administered daily over the period of time which the medical sedation takes place. In some embodiments, the medical sedation of the Neuroquiescence Protocol may be a deep sedation, or may be a general anesthesia, so long as the sedation is sufficient to pause bioelectrical activity, such as abnormal bioelectrical activity, of neurons in a subject with a disorder associated with neurological bioelectrical dysfunction, such as epilepsy or suffering from seizures associated with epilepsy.

In some embodiments, the disorder associated with neurological bioelectrical dysfunction may be seizures associated with epilepsy, such as epilepsy with generalized tonic-clonic seizures, epilepsy with myoclonic absences, frontal lobe epilepsy, temporal lobe epilepsy, benign rolandic epilepsy (BRE), childhood absence epilepsy (CAE), juvenile myoclonic epilepsy (JME), benign occipital epilepsy, Lennox-Gastaut syndrome (LGS), "genetic" or "mitochondrial" epilepsy, SCN2A encephalopathy, Landau-Kleffner Syndrome, Ohtahara syndrome, Rasmussen's syndrome, West's syndrome, Rett syndrome, CDKL5 disorder, essential tremor, Dravet syndrome, Doose syndrome, acute repetitive seizures, status epilepticus, refractory status epilepticus, super-refractory status epilepticus (SRSE), PCDH19 pediatric epilepsy, increased seizure activity, and breakthrough seizures.

In embodiments of the inventive concept, the subject may be a human subject. Human subjects of any gender (for example, male, female or transgender) and at any stage of development (i.e., neonate, infant, juvenile, adolescent, adult, elderly) diagnosed with, for example, a seizure associated with epilepsy, may be treated according to the methods and protocols of the present inventive concept.

Dosages to medically sedate the subject are not particularly limited, so long as the sedation, and pausing of bioelectrical activity of neurons are maintained by the dosage. In some embodiments, midazolam is administered to the subject at a dosage of about 0.2, 0.3, 0.4, 0.5, or 0.6 mg/kg. Similarly, the rate of administration, for example, intravenous administration, is not particularly limited, so long as the desired effect, e.g., pausing of bioelectrical activity to avail healing, is achieved and/or maintained. In some embodiments, midazolam is administered at a rate of about 0.5, 1.0, 2.0, 3.0, 4.0, or 5.0 mcg/kg/min.

In other embodiments of the present inventive concept, the anesthetic may be administered for a second period at a time after the first or initial period of medical sedation. In some embodiments, the second period of medical sedation takes place about 4, 5, 6, 7, 8, 9, or 10 weeks after the first or initial period of medical sedation. In some embodiments, the second period of medical sedation takes place about 6 weeks after the first or initial period of medical sedation. In some embodiments, the second period of medical sedation takes place about 9 weeks after the first or initial period of medical sedation.

In yet other embodiments, Neuroquiescence may be induced in conjunction with administering of additional medications useful in treating or preventing seizures associated with an epileptic disorder, or treating or preventing irregular, abnormal, or excessive neuronal activity. For example, Neuroquiescence may be induced in conjunction with a therapeutically effective amount of a medication to induce vasodilation, oxygenation, and/or to reduce inflammation before, during, and/or after medical sedation of the subject. The medication to induce vasodilation, oxygenation, and/or to reduce inflammation is not particularly limited, and may be any that would be appreciated by one of skill in the art.

Neuroquiescence may be followed, in some embodiments, by monitoring of bioelectrical activity of neurons by monitoring bioelectrical activity, for example, on an electroencephalogram (EEG), and/or with functional magnetic resonance imaging (fMRI), or by any method of monitoring bioelectrical activity of neurons as would be appreciated by one of skill in the art.

In still other embodiments of the present inventive concept, Neuroquiescence may be induced in conjunction with administration of a therapeutically effective amount of a medication that can induce vasodilation, oxygenation, and/or reduction of inflammation. The medication may by administered prior to, during, and/or after a medical sedation/Neuroquiescence session. The medication that is administered and the route of administration of the medication to induce vasodilation, oxygenation, and/or reduction of inflammation is not particularly limited, and may be any that would be envisioned by one of skill in the art.

In some embodiments of the present inventive concept, the use of vasodilation with oxygenation medications would enable even conventional existing antiseizure medications to better do what they do, for example, as a temporary solution until these patients can be engaged with Neuroquiescence, for example, for those patients who are said to be "resistant," i.e., not responsive to conventional existing antiseizure medications.

In other embodiments of the present inventive concept, the use of vasodilation and oxygenation for neonates can disrupt the typical flow of "genetic or mitochondrial epilepsy" seizures or infantile spasms. The use of vasodilation as preemptive care should become standard when brainscans and bloodflow scans or genetic testing indicate the need. In some embodiments, a vasodilation medication may be used to improve bloodflow in the brain as a preemptive treatment or a mitigation of infantile spasms.

In some embodiments of the present inventive concept, the medication to induce vasodilation is Prostin. In some embodiments, the medication to induce vasodilation is Dobutamine.

In other embodiments of the present inventive concept, Neuroquiescence may be used in addition to existing immunoinflammatory medications. In some embodiments, the immunoinflammatory medication may be a tumor necrosis factor (TNF) inhibitor, for example, etanercept (ENBREL®). In some embodiments, the etanercept is administered perispinally.

In other embodiments, use of a vasodilation medication to improve cerebrovascular bloodflow to microvessels avails transport capacities of medications to bioelectrically agitated neurons. Vascular dilation to improve cerebrovascular bloodflow improves access for any vascular transported medications to neurons and is nearly always required as a preparation for the sedation phase of Neuroquiescence to enable glial cells their neuronal repairs. This applies beyond neurons in the brain to include motor neurons and sensory neurons to include seizures associated with epilepsy, such as, (Benign Rolandic Epilepsy of Childhood, Absence Epilepsy, Juvenile Myoclonic Epilepsy, Benign Occipital Epilepsy, Lennox-Gastaut syndrome, "genetic" or "mitochondrial" epilepsy); nervous system neuropathy such as Neuropathic Pain, Fibromyalgia, Essential Tremors, Blepharospasm, Nystagmus, Tinnitus, Auditory Neuropathy, Phantom-limb Pain, Involuntary Movement or motor neuron dysregulations, Lewy body Dementia, Alzheimer's, and Cluster Headaches; and infantile spasms, such as Auditory Agnosia, Stuttering of Speech, involuntary movements or loss of muscular control, are considered within the scope of the present inventive concept.

Exemplary aspects of the present inventive concept will be further described as follows.

I. Vasodilation as Prophylaxis for Infantile Spasms and Epilepsy

The protocol of the present inventive concept includes prophylaxis to identify and avoid ever having even the first seizure. Exemplary is a toddler who had low bloodflow in the left hemisphere, exhibiting symptoms of Infantile Spasms, and had neuronal agitation which surely would have interconnected enough to cause seizures (see, EXAMPLES, Case Example JH). The chosen medication for vasodilation is Prostin or Dobutamine; after three days the neuronal agitation noise ended; after three months, bloodflow in the left hemisphere was robust; after six months, previous left-hemisphere malformations were approaching normal. We never needed the Neuroquiescence session of sustained sedation as was needed for those who already had progressed to seizures.

We envision in the future where all neonates are checked for robust cerebral hemodynamics and mitigated to overwhelm any genetic risks that would have them on a trajectory toward Epilepsy or Infantile Spasm symptoms from deficient neuronal oxygenation that worsens during sleep.

We advocate using fMRI for inspecting neonatal cerebrovascular bloodflow and mitigating those having less than robust bloodflow and oxygenation. This is especially important for neonates who experienced transient hypoglycemia or transient restriction in oxygenation or bloodflow.

Stuttering of speech is a timing maladaptation due to low cerebrovascular bloodflow between brain regions involved in motor-control required for actuating words, and among the symptoms of Infantile Spasms. Vasodilation and oxygenation improvements may resolve stuttering without requiring a Neuroquiescence session pausing of bioelectrical activity.

H. Neuroaquiescence for Epilepsy in Children

The workflow for the Neuroquiescence Protocol will require neurology and anesthesiology expertise. Under no circumstances should anyone without this expertise pursue using the information described here.

All Neuroquiescence Protocol procedures for epilepsy are performed only following analysis of patient seizure activity and nervous system bioelectrical dysregulation. Preliminary work is essentially the same as though we were considering brain surgery, so the reader is presumed to understand this workflow as a starting-point to understanding Neuroquiescence.

Patient Baseline Examination

In embodiments of the present inventive concept, a patient baseline examination may include evaluation of patient: mental status; HEENT (head, ears, eyes, nose, throat); heart; lungs; extremities; neurovascular indication; inflammation; oxygenation graft type-E measurement; seizure rate and quantity, time of day or night, associated activities; antiseizure medications; allergies; trauma; air quality and other environmental exposures; blood-oxygen levels; diabetes and glucose levels and sensitivities or hypoglycemia; loss of consciousness; sleepiness; fever; infantile spam symptoms (bedwetting, stuttered speech, auditory agnosia); tumor; electrolyte abnormality; metabolic or hepatic or renal failure; hypoxia; hyperthermia; blood-pressure hypotension; pediatric assessment triangle (appearance, breathing effort or work of breathing); and brainscans, for example, fMRI, EEG, ECG, oxygenation, and cerebral CT bloodflow scanning.

Neonatal and Special-Needs Children

Special needs children and neonatal diagnostic assessment may require continued use of Pediatric based treatment protocol regardless of age and weight.

Neonatal Seizure

| Etiology | Time Onset |
| --- | --- |
| Hypoxic ischemic encephalopathy | 12-24 hour |
| Drug withdrawal | 24-72 hour |
| Hypocalcemia (nutritional) | 3-7 days |
| Aminoaciduria/organic aciduria | 3-7 days |

The order of the assessment and treatment may require alteration to accommodate the developmental status of the pediatric patient. Neonates, infants and toddlers should never be separated from the caregiver during assessments or when alert during treatments.

The following chart defines week six as the week of meaningful sedation has been the most used approach, but by waiting until the cerebrovascular bloodflow is robust, we optimize the timing of meaningful sedation and reduce likelihood of return of neuronal agitation, and therefore an additional sedation session.

| Week of Robust cerebrovascular bloodflow | Week of Neuroquiescence | Ending for Dobutamine & counterinflammatory rotation |
| --- | --- | --- |
| Week four or sooner | Week six | Week twelve |
| Week five | Week seven | Week fourteen |
| Week six | Week nine | Week seventeen |
| Week eight | Week twelve | Week twenty-one |
| Week ten | Week sixteen | Week twenty-six |

Establish an fMRI perspective on cerebrovascular bloodflow from week zero and observe changes with the Dobutamine and the alternating weeks of counterinflammatory/anti-neuroinflammation medications. Document at which week cerebrovascular bloodflow appears robust. Wait the additional weeks designated in the chart for the week of Neuroquiescence sustained sedation. Bloodflow should be stable, not improving because it was noted as robust, and not degrading in robustness.

Sedation sessions longer than six days have been used when neuroinflammation was slow to subside given the medications approved for use with children. If a patient is already sedated in a Neuroquiescence session to prevent seizures, the meaningful week begins only after cerebrovascular bloodflow becomes robust by the extra margin designated in the chart.

While nearly all children were ready and responsive in week-six, teenagers who had unmanageable seizures since they were infants required more time for cerebral bloodflow to become robust. These teenagers (the most challenging cases we could find in our Children's hospital search) would have continued to have seizures even after the Dobutamine began in week-one, so their Neuroquiescence session was extended to be sustained for these weeks.

Separately from using extended Neuroquiescence for avoiding the withdrawal sickness or seizures, six days of sustained sedation appeared to be the point of diminishing returns for neuronal healing. If neuronal agitation later returned, there were other impediments to robust oxygenation of those neurons, such as inflammation. (Lung oxygenation issues and dysregulated pancreas issues were rare examples of impediments to resolving neuronal agitation.) If cerebrovascular bloodflow is not robust, transport to microvessels of even the anesthesia is constricted, so the bioelectrical activity of those neurons may not be paused as required for their repair. First achieving robust cerebral bloodflow therefore increases the likelihood of success with a single (six-day) sedation session.

III. Neuroquiescence for Epilepsy in Adults

Adult Epilepsy differs from Children's Epilepsy in that there may be more neurophysiological trauma and neuroinflammation, perhaps more influence from diabetes or previous surgeries. To enable Neuroquiescence the best potential for success, we must resolve impediments to robust cerebrovascular bloodflow and have stable glucose levels.

A medication we use for neuroinflammation is Neurokinin-2 delivered by IV, and we do not combine this with Dobutamine. We alternate weeks between the Neurokinin-2 (Nk2) versus the Dobutamine Infusion (Dob). We are limited to four doses of Neurokinin 2, so we distribute them among the Dobutamine doses to maximize the Neurokinin-2 counterinflammation. We use no Dobutamine on the day before or after the day of Neurokinin-2.

The preparation phase for Adult Epilepsy is therefore longer than the preparation phase for Children's Epilepsy. Rather than the typical week for the Neuroquiescence sedation being week six as for children, the meaningful sedation for adults is typically in week nine.

| Nk2 vs Dob | Day 1 | Day 2 | Day 3 | Day 4 | Day 5 | Day 6 | Day 7 |
|---|---|---|---|---|---|---|---|
| Week 1 | Dob | Dob | Dob | Dob | Dob | Dob | none |
| Week 2 | Nk2 | none | Dob | Dob | Dob | Dob | Dob |
| Week 3 | Dob | Dob | Dob | Dob | Dob | Dob | none |
| Week 4 | Nk2 | none | Dob | Dob | Dob | Dob | Dob |
| Week 5 | Dob | Dob | Dob | Dob | Dob | Dob | none |
| Week 6 | Nk2 | none | Dob | Dob | Dob | Dob | Dob |
| Week 7 | Dob | Dob | Dob | Dob | Dob | Dob | none |
| Week 8 | Nk2 | none | Dob | Dob | Dob | Dob | Dob |

-continued

| Nk2 vs Dob | Day 1 | Day 2 | Day 3 | Day 4 | Day 5 | Day 6 | Day 7 |
|---|---|---|---|---|---|---|---|
| Week 9 | Dob | Dob | Dob | Dob | Dob | Dob | Dob |
| Week 10 | Dob | Dob | Dob | Dob | Dob | Dob | Dob |

| Week of Robust cerebrovascular bloodflow | Week of Neuroquiescence | Ending for Dobutamine & counterinflammatory rotation |
|---|---|---|
| Week six or sooner | Week nine | Week fifteen |
| Week eight | Week eleven | Week nineteen |
| Week ten | Week fourteen | Week twenty-four |
| Week twelve | Week seventeen | Week twenty-nine |
| Week fourteen | Week twenty | Week thirty-four |

TABLE I.

Children Epilepsy Protocol Chart

| Function | Medication | Week One | Pre-Neuroquiescence | Neuroquiescence Sedation Session | Post-Neuroquiescence |
|---|---|---|---|---|---|
| Anesthesia Allergy Test | Midazolam preferred | day one | | | |
| Anesthesia Allergy Test | Fentanyl | if allergic to Midazolam | | | |
| Sedation (Anesthesia) (IV) | Midazolam (continuous infusion) | 6 days sustained | | 6 days sustained | |
| Sedation (Anesthesia) (IV) | Fentanyl (continuous infusion) | alternative | | alternative | |
| Remove Antiseizure Meds | all antiseizure meds including CBD | Sedation assisted | | | |
| Vasodilation | Dobutamine (preferred) | low dosage | normal dosage | normal dosage | normal dosage |
| Vasodilation | Prostin (special cases) | low dosage | normal dosage | normal dosage | Dobutamine |
| Measure Blood-Oxygen levels | case & situation-specific oxygenation | | | | |
| Oxygenation (inhalation mask) | Ipratropium (anticholinergic - if needed) | | during sedation | | during sedation |
| Oxygenation (inhalation mask) | Tiotropium (anticholinergic - if needed) | | during sedation | | during sedation |
| Oxygenation (inhalation mask) | Aclidinium (anticholinergic - if needed) | | during sedation | | during sedation |
| Oxygenation (short duration) | Albuterol (bronchial relaxant) | | constant IV | | constant IV |
| Oxygenation (short-duration) | Levalbuterol (bronchial relaxant) | | constant IV | | constant IV |
| Oxygenation (long-duration) | Arformoterol (respiratory impairments) | | | twice daily | twice daily |
| Oxygenation (long-duration) | Salmeterol (respiratory impairments) | | | twice daily | twice daily |
| Oxygenation (long-duration) | Xanthine (respiratory impairments) | | | twice daily | twice daily |
| Oxygenation (long-duration) | Indacaterol (respiratory impairments) | | | twice daily | twice daily |
| Oxygenation (long-duration) | Formoterol (respiratory impairments) | | | twice daily | twice daily |
| Oxygenation (long-duration) | Vilanterol (respiratory impairments) | | | twice daily | twice daily |
| Immunoinflammatory | Cyclophosphamide (Cytoxan) | twice daily | | | twice daily |
| Immunoinflammatory | Ketoprofen | | twice daily | twice daily | |
| Amino Acid Supplement | IV or Oral | daily | daily | daily | daily |

TABLE II

Midazolam Deep-Quiet Chart
Midazolam extended sedation deep-quiet session

| Bodyweight First Dose | Day one of sedation 0.5 mcg/kg/minute | Day two of sedation 1 mcg/kg/minute | Day three of sedation 2 mcg/kg/minute | Day four of sedation 3 mcg/kg/minute | Day five of sedation 4 mcg/kg/minute | Day six of sedation 5 mcg/kg/minute |
|---|---|---|---|---|---|---|
| 5 kg | 0.15 mL per hour | 0.3 mL per hour | 0.6 mL per hour | 0.9 mL per hour | 1.2 mL per hour | 1.5 mL per hour |
| 10 kg | 0.3 mL per hour | 0.6 mL per hour | 1.2 mL per hour | 1.8 mL per hour | 2.4 mL per hour | 3.0 mL per hour |
| 15 kg | 0.45 mL per hour | 0.9 mL per hour | 1.8 mL per hour | 2.7 mL per hour | 3.6 mL per hour | 4.5 mL per hour |
| 20 kg | 0.6 mL per hour | 1.2 mL per hour | 2.4 mL per hour | 3.6 mL per hour | 4.8 mL per hour | 6.0 mL per hour |
| 25 kg | 0.75 mL per hour | 1.5 mL per hour | 3.0 mL per hour | 4.5 mL per hour | 6.0 mL per hour | 7.5 mL per hour |
| 30 kg | 0.9 mL per hour | 1.8 mL per hour | 3.6 mL per hour | 5.4 mL per hour | 7.2 mL per hour | 9.0 mL per hour |
| 35 kg | 1.05 mL per hour | 2.1 mL per hour | 4.2 mL per hour | 6.3 mL per hour | 8.4 mL per hour | 10.5 mL per hour |
| 40 kg | 1.2 mL per hour | 2.4 mL per hour | 4.8 mL per hour | 7.2 mL per hour | 9.6 mL per hour | 12.0 mL per hour |

TABLE II-continued

Midazolam Deep-Quiet Chart
Midazolam extended sedation deep-quiet session

| Bodyweight First Dose | Day one of sedation 0.5 mcg/kg/minute | Day two of sedation 1 mcg/kg/minute | Day three of sedation 2 mcg/kg/minute | Day four of sedation 3 mcg/kg/minute | Day five of sedation 4 mcg/kg/minute | Day six of sedation 5 mcg/kg/minute |
|---|---|---|---|---|---|---|
| 45 kg | 1.35 mL per hour | 2.7 mL per hour | 5.4 mL per hour | 8.1 mL per hour | 10.8 mL per hour | 13 mL per hour |
| 50 kg | 1.50 mL per hour | 3.0 mL per hour | 6.0 mL per hour | 9.0 mL per hour | 12.0 mL per hour | 15 mL per hour |
| 55 kg | 1.65 mL per hour | 3.3 mL per hour | 6.6 mL per hour | 9.9 mL per hour | 13.2 mL per hour | 16.5 mL per hour |
| 60 kg | 1.8 mL per hour | 3.6 mL per hour | 7.2 mL per hour | 1.08 mL per hour | 14.4 mL per hour | 18.0 mL per hour |

Having described various aspects of the present inventive concept, the same will be explained in further detail in the following examples, which are included herein for illustration purposes only, and which are not intended to be limiting to the inventive concept.

EXAMPLES

We have had approximately 200 cases between the two hospitals using the protocol to resolve epilepsy. We deliberately sought out difficult cases, which was the reason for adding the second hospital in a large city. There were over twenty patients living in the hospital because their seizures were so uncontrollable and risky. All of these patients were resolved of their seizures, so we sought teenagers to be brought into the hospital. In all, three cases of epilepsy of the approximately 200 are not resolved. A fourth has diabetes which is the root-cause of the seizures and must be resolved before we can heal the neuronal connections causing the seizures.

Case Example: JH

An age eight-months baby presented brain malformation and diminished oxygenation and bloodflow in the left hemisphere.

Parents noted at four months abnormal movements which we attribute to muscular spasms, especially for the left hand. EEG measurement indicated monomorphic high amplitude neuronal activity, but not interconnected with a region that would trigger seizures.

In this case we used for treatment only Vasodilation Pediatric Prostin VF—0.05-01 mcg/kg/min IV initially at week one and usual maintenance ranges from 0.01-0.4 mcg/kg/min for six weeks.

All symptoms of Infantile Spasms were resolved. EEG measurements became normal within three days, and cerebral bloodflow measurements became normal within six weeks.

To assist with good neurovascular healing, the patient had twice daily IV sessions of vasodilation medication, oxygenation medication, and an amino acid for approximately one year. EEG measurements were made for one hour during the twice-daily IV medications. fMRI brainscans and measurements of cerebral bloodflow were scheduled twice per week for the first year, and once each month thereafter along with an EEG measurement session.

Case Example: JAS

An age nine-months baby presented recurrent seizures twice daily as left hemisphere focal brain agitation bioelectrical activity. She had her first convulsive episode at age of two months during a febrile illness.

There is a family history, a cousin with a history of "grand mal" seizures who died at age 3. A well-nourished infant, she presented inconsolable irritability requiring attention. She had a history of attempts with ineffective antiseizure medications.

Cerebral bloodflow was within normal ranges. During sleep, EEG amplitudes indicated epileptic levels of bioelectrical activity exceeding 85% of spatial tracing. The brain imaging revealed a ventricular enlargement center of high amplitude bioelectrical activity. She had a radiation session which presented good prognostic following the ventricular embolism surgical intervention with easy access.

In this case we used for treatment Vasodilation Pediatric Prostin VF—0.05-01 mcg/kg/min by IV initially at week one. Usual maintenance ranges from 0.01-0.4 mcg/kg/min for six weeks.

As with all children, in all cases, we removed all antiseizure medications.

Daily Amino Acid 12 mcg/kg (maximum dose) for six weeks. Daily Glucosamine oral supplements for children; (the glucosamine was later removed from the protocol).

Midazolam continuous infusion initially 50-100 mcg/kg IV over 2-3 minutes, repeat q2-3 min PR. Required up to 600 mcg/kg total dose; we did not exceed 6 mg total dose for four days. Neuroquiescence sessions with Midazolam were repeated twice before showing total improvement and healing. All symptoms of seizures and agitated bioelectrical brain activity were resolved. EEG monitoring and Brainscans became normal and her learning assessments are considered developmentally good.

Case Example: LIL

A child of age four-years with episodes of "blanking-out" has episodes in which abruptly stops all activity for 10 seconds, followed by a rapid return to full consciousness. Her eyes are open during the episodes and she remains motionless with occasional hand movements.

History of previous ineffective antiseizure medications was Tegretol for 2 years. Radiologic brain examination revealed epileptic activity in sleep time. Normal cerebral blood flow (CBF).

General physical examination revealed an allergy for Midazolam. In this case we used for treatment Fentanyl as an alternative medication for Neuroquiescence.

We investigated her bloodflow and oxygenation with brainscans during her sleep, and we found normal cerebral bloodflow, but low oxygen levels in the brain. As such, Prostin was used as the vasodilator for assisting the microvessels.

Vasodilation Pediatric Prostin VF—0.05-01 mcg/kg min IV initially at week one. Usual maintenance ranges from 0.01-0.4 mcg/kg/min for six weeks.

All antiseizure medications were removed. Daily Amino Acid 12 mcg/kg (maximum dose) for six weeks. Daily Glucosamine oral supplements for children; (we later removed glucosamine from the protocol).

Fentanyl premedication 0.5-2 mcg/kg IV gives 3 minutes prior the anesthesiologist proceeded for the more maximum safe dosage on keeping her for continuous sedation. After premedication we adjusted Fentanyl dosage 2-3 mcg/kg IV/IMq1-2 hr PRN. We did not exceed 6 mg total dose for six days. Neuroquiescence with Fentanyl was repeated for three sessions before showing total improvement and healing.

All symptoms of noisy bioelectrical brain activity after Neuroquiescence were resolved. EEG monitoring and brain-scans became normal and her learning assessment post-treatment are considered appropriated for her age.

Case Example: REM

An age eleven-months baby presented with low neuronal agitation recurrent from the left hemisphere.

The first EEG-measured bioelectrical agitation was measured at age four months. There were no seizures, but antiseizure medication had been attempted to resolve the agitated neurons to prevent seizures.

General physical examination revealed a well-nourished infant with normal baseline oxygenation measurement and cerebral bloodflow.

The neurological examination revealed an alert infant. Radiologic brain imagining examination revealed low-amplitude agitation activity especially during sleep.

In this case we used for treatment only Vasodilation Pediatric Prostin VF—0.05-01 mcg/kg min IV initially at week one. Usual maintenance ranges from 0.01-0.4 mcg/kg/min for six weeks.

We removed all previous antiseizure medications (which were GABA-based).

Daily Amino Acid 12 mcg/kg (maximum dose) for six weeks, and Daily Glucosamine oral supplements for children. (The glucosamine was later discontinued from the protocol.)

All symptoms of bioelectrical agitation activity were resolved following the vasodilation treatment, so in this case there was no need for a Neuroquiescence session.

EEG monitoring and brainscans became normal and his learning and interaction assessment post-treatment are considered normal for his age.

Case Example: BAR

An age three-years boy was presented to his pediatrician with a history of new-onset headaches accompanied by nausea lasting for several hours daily. The neurological examination was normal, and migraine was initially suspected.

After symptoms persisted for two weeks, he presented refractory seizures that began with his typical aura followed by lip-smacking and left-hand automatisms; the right-hand had a tonic posture. He had a brief post-ictal aphasia.

Cranial magnetic resonance imaging (MRI) revealed a cerebral mass located in the pineal region measuring 1×2.2× 2.5 cm. The tumor displayed dorsal cystic structures and a ventral solid portion with inhomogeneous contrast agent enhancement leading to a compression of the tectum. The consecutive aqueduct stenosis resulted in occlusive hydrocephalus. ventriculostomy of the third ventricle was performed to reduce intracranial pressure.

Tumor markers such as cavernous angioma in serum and cerebrospinal fluid (CSF) were within the normal range.

We oversaw the patient through a total tumor resection through a suboccipital supra cerebellar approach. Postoperative imaging demonstrated complete reception. Postoperative clinical examination, the boy was found to have several episodes of seizures per day recurrent from both hemispheres and high bioelectrical agitation measured with EEG.

In this case we used for treatment Vasodilation Pediatric Prostin VF—0.05-01 mcg/kg min IV initially at week one. Usual maintenance ranges from 0.01-0.4 mcg/kg/min for six weeks.

Daily Amino Acid 12 mcg/kg (maximum dose) for six weeks.

Daily Glucosamine oral supplements for children (which is no longer in the protocol).

Anti-inflammatory medications from week one per the standard alternating weeks.

As for all children, in all cases, all antiseizure medications were removed.

Neuroquiescence with Midazolam continuous infusion initially 50-100 mcg/kg IV over 2-3 minutes, repeat q2-3 min PR. Required up to 600 mcg/kg total dose; we did not exceed 6 mg total dose for seven days. Neuroquiescence with Midazolam was repeated several seven-day-sessions before showing an improvement in his noisy bioelectrical brain activity.

All symptoms of seizures and bioelectrical brain activity after Neuroquiescence showed a partial improvement. He has continuous treatment, EEGs, Brainscans and fMRI.

Neuroinflammation is the likely impediment to healing. The next step is to use a stronger anti-inflammation medication, which will require permission for a trial inasmuch as it is not presently approved for children.

Example Case: STEH

Early encephalopathy, beginning in the first month of life, associated with inborn errors of metabolism by hyperglycemia. Ineffective antiseizure medications and treatments fill his 14 years of life.

Family history notes that his father had similar episodes as a child.

Radiologic brain examination revealed epileptic activity. Normal cerebral blood flow (CBF). EEG epileptic activity exceeding spatially 90% of the tracing, especially under photo stimulation. The brain imaging revealed a moderately-high amplitude of agitated bioelectrical activity. He had severe myoclonus, focal and tonic crises.

In this case we used for treatment Vasodilation Prostin VF—0.05-01 mcg/kg min IV initially at week one. Usual maintenance ranges from 0.01-0.4 mcg/kg/min for six weeks. We removed all antiseizure medications.

Daily Amino Acid 12 mcg/kg (maximum dose) for six weeks.

Daily Glucosamine oral supplements for children

Anti-inflammation medication per the standard schedule in alternating weeks.

Neuroquiescence with Midazolam continuous infusion initially 50-100 mcg/kg IV over 2-3 minutes, repeat q2-3 min PR. Required up to 600 mcg/kg total dose; we did not exceed 6 mg total dose for seven days. Neuroquiescence with Midazolam was repeated for two sessions before showing total improvement and healing.

All symptoms of seizures and bioelectrical brain activity were resolved after Neuroquiescence. EEG monitoring and Brainscans became normal and his learning assessment post-treatment are considered normal.

His psychological assessment revealed a continuous behavioral maladaptation to pretend to exhibit the symptoms as when he had seizures, but only when his mother is present. He performs for her even though we can see on EEG that not only has he no seizure, he has no neuronal agitation. We expected to see this in some older patients, and we did. With Neuroquiescence able to resolve seizures and completely heal epilepsy, developmental psychology will be needed for helping minds that never developed emotionally and/or intellectually to their genetic potential.

While specific embodiments of the present inventive concept have been shown and described, it will be understood that other modifications, substitutions and alternatives are apparent to one of ordinary skill in the art. Such modifications, substitutions and alternatives can be made without departing from the spirit and scope of the inventive concept, which should be determined from the appended claims.

That which is claimed:

1. A method for treating or preventing seizures associated with an epileptic disorder in a subject in need thereof comprising:
   medically sedating the subject for a sustained period of time by administering a therapeutically effective amount of an anesthetic,
   wherein sedating the subject pauses bioelectrical activity of neurons in the subject to facilitate healing of the neurons in the subject.

2. The method of claim 1, wherein medically sedating the subject enables glial cell biomechanisms for neuronal healing, remyelination, pruning, and/or disconnecting of maladapted circuits formed due to agitated neurons.

3. The method of claim 1, wherein the subject is further administered a therapeutically effective amount of a medication to induce vasodilation, oxygenation, and/or reduction of inflammation in the subject prior to, during, and/or after medical sedation.

4. The method of claim 1, wherein the subject is medically sedated continuously for a minimum of 3 days.

5. The method of claim 1, wherein the anesthetic is administered to the subject by intravenous infusion.

6. The method of claim 1, wherein the anesthetic is midazolam, or a pharmaceutically acceptable salt thereof.

7. The method of claim 1, wherein the subject is a human subject.

8. The method of claim 7, wherein the human subject is a neonate, infant, juvenile, or adolescent human subject.

9. The method of claim 7, wherein the human subject is an adult.

10. The method of claim 1, wherein the pausing of bioelectrical activity is monitored by an electroencephalogram (EEG) and/or by functional magnetic resonance imaging (fMRI).

11. A method for treating or preventing irregular, abnormal, or excessive neuronal activity in a subject in need thereof comprising:
    medically sedating the subject for a sustained period of time by administering a therapeutically effective amount of an anesthetic,
    wherein the sedating of the subject pauses bioelectrical activity of neurons in the subject to facilitate healing of the neurons.

12. The method of claim 11, wherein medically sedating the subject enables glial cell biomechanisms for neuronal healing, remyelination, pruning, and/or disconnecting of maladapted circuits formed due to agitated neurons.

13. The method of claim 11, wherein the subject is further administered a medication to induce vasodilation, oxygenation, and/or reduction of inflammation in the subject prior to, during, and/or after medical sedation.

14. The method of claim 11, wherein the subject is medically sedated continuously for a minimum of 3 days.

15. The method of claim 11, wherein the anesthetic is administered to the subject by intravenous infusion.

16. The method of claim 11, wherein the anesthetic is midazolam, or a pharmaceutically acceptable salt thereof.

17. The method of claim 11, wherein the subject is a human subject.

18. The method of claim 17, wherein the human subject is a neonate, infant, juvenile, or adolescent human subject.

19. The method of claim 17, wherein the human subject is an adult.

20. A method of pausing bioelectrical activity in neurons in a subject suffering from an epileptic disorder comprising:
    medically sedating the subject for a sustained period of time by administering a therapeutically effective amount of an anesthetic,
    wherein the pausing of bioelectrical activity facilitates healing of neurons exhibiting irregular, abnormal, and/or excessive activity.

* * * * *

UNITED STATES PATENT AND TRADEMARK OFFICE
CERTIFICATE OF CORRECTION

| | |
|---|---|
| PATENT NO. | : 10,716,792 B2 |
| APPLICATION NO. | : 16/698444 |
| DATED | : July 21, 2020 |
| INVENTOR(S) | : Gary Aaron Howard and Debora Zucco Sassi Yonezawa Siviglia |

It is certified that error appears in the above-identified patent and that said Letters Patent is hereby corrected as shown below:

On the Title Page

Item (56) - Other Publications, Column 2, Line 34, (approx.):
Change "Todididk et al." to -- Tobinick --.

In the Specification

Column 11, Line 11:
Change "H." to -- II. --.

Signed and Sealed this
First Day of September, 2020

Andrei Iancu
*Director of the United States Patent and Trademark Office*